United States Patent
Swanson

(10) Patent No.: US 8,892,206 B1
(45) Date of Patent: Nov. 18, 2014

(54) CLOSED-LOOP DEEP BRAIN STIMULATION SYSTEM ADAPTED TO ACCOMMODATE GLIAL SCARRING AND METHOD OF OPERATION

(75) Inventor: John W. Swanson, Portland, OR (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 1728 days.

(21) Appl. No.: 11/877,275

(22) Filed: Oct. 23, 2007

Related U.S. Application Data

(60) Provisional application No. 60/862,915, filed on Oct. 25, 2006.

(51) Int. Cl.
*A61N 1/36* (2006.01)

(52) U.S. Cl.
USPC .......................................................... 607/45

(58) Field of Classification Search
USPC .................. 607/28, 45, 115, 116; 606/32
See application file for complete search history.

(56) References Cited

U.S. PATENT DOCUMENTS

| | | | | |
|---|---|---|---|---|
| 5,769,880 | A * | 6/1998 | Truckai et al. | 607/101 |
| 6,620,186 | B2 * | 9/2003 | Saphon et al. | 607/1 |
| 6,647,289 | B2 * | 11/2003 | Prutchi | 600/547 |
| 6,922,590 | B1 * | 7/2005 | Whitehurst | 607/45 |
| 2004/0133248 | A1 * | 7/2004 | Frei et al. | 607/45 |
| 2005/0119703 | A1 * | 6/2005 | DiLorenzo | 607/2 |
| 2006/0149337 | A1 * | 7/2006 | John | 607/45 |
| 2006/0173509 | A1 * | 8/2006 | Lee et al. | 607/45 |
| 2006/0173510 | A1 * | 8/2006 | Besio et al. | 607/45 |
| 2006/0224222 | A1 * | 10/2006 | Bradley et al. | 607/116 |
| 2006/0229686 | A1 * | 10/2006 | Giftakis et al. | 607/45 |
| 2007/0067002 | A1 * | 3/2007 | Lozano | 607/45 |

OTHER PUBLICATIONS

National Institute of Neurological Disorders and Stroke "Parkinson's Disease Backgrounder" 2004.*
Fitch, et al., "Cellular and Molecular Mechanisms of Glial Scarring and Progressive Cavitation: In Vivo and In Vitro Analysis of Inflammation-Induced Secondary Injury after CNS Trauma", The Journal of Neuroscience, Oct. 1, 1999, 19(19):8182-8198.

* cited by examiner

*Primary Examiner* — Kennedy Schaetzle
*Assistant Examiner* — Erica Lee

(57) ABSTRACT

In one embodiment, a deep brain stimulation (DBS) system for electrically stimulating a target location in the brain of a patient, comprises: pulse generating circuitry for generating electrical pulses; at least one electrical lead for conducting electrical pulses generated by the pulse generating circuitry to the target location using one or several stimulation electrodes, wherein the at least one electrical lead further comprises one or several electrochemical sensors for sensing an extracellular level of one or several neurotransmitters and/or precursors; and a controller for controlling the pulse generating circuitry using closed-loop feedback based upon the extracellular level of the one or several neurotransmitters, wherein the controller for controlling the pulse generating circuitry processes the extracellular level of the one or several neurotransmitters using a measured impedance between one or several of the electrochemical sensors and a reference electrode.

10 Claims, 2 Drawing Sheets

CLOSED-LOOP DEEP BRAIN STIMULATION SYSTEM ADAPTED TO ACCOMMODATE GLIAL SCARRING AND METHOD OF OPERATION

RELATED APPLICATIONS

This application claims the benefit of U.S. Provisional Application No. 60/862,915, filed Oct. 25, 2006, the disclosure of which is fully incorporated herein.

BACKGROUND

The present application is generally related to controlling deep brain stimulation using a closed-loop system that compensates for changes in sensor sensitivity for neurotransmitter levels that result from glial scarring.

Deep brain stimulation (DBS) refers to the delivery of electrical pulses into one or several specific sites within the brain of a patient to treat various neurological disorders. For example, DBS has been proposed as a clinical technique for treatment of chronic pain, essential tremor, Parkinson's disease (PD), dystonia, epilepsy, depression, obsessive-compulsive disorder, and other disorders.

A DBS procedure typically involves first obtaining preoperative images of the patient's brain (e.g., using computer tomography (CT) or magnetic resonance imaging (MRI)). The imaging process sometimes involves first affixing to the patient's skull fiducial markers that are discernable on the images produced by the imaging process. The fiducial markers assist in registering the preoperative images to the actual physical position of the patient in the operating room during the subsequent surgical procedure. Using the preoperative images, the neurosurgeon can select a target region within the brain, an entry point on the patient's skull, and a desired trajectory between the entry point and the target region. The entry point and trajectory are carefully selected to avoid intersecting or otherwise damaging critical brain structures.

In the operating room, the patient is immobilized and the patient's actual physical position is registered. The physician marks the entry point on the patient's skull and drills a burr hole at that location. A mechanism is provided to precisely control the path through the patient's brain to the desired location. Specifically, a positioning error on the order of a millimeter can have a significant negative effect on the efficacy of the DBS therapy. Stereotactic instrumentation and trajectory guide devices are commercially available products that facilitate the control of the trajectory and positioning of a lead during the surgical procedure.

A microdrive introducer can be used to insert a deep brain stimulation lead toward the selected region of the brain along the selected trajectory. The lead provides one or several conductive paths to deliver stimulation pulses to the selected region. The lead includes a very small diameter insulative lead body with one or several conductors (e.g., stranded wires) embedded in the insulative material. The lead also includes one or several electrodes at a distal end of the lead that are electrically coupled to respective conductors. The electrodes can be used to record signals within the brain and/or to deliver electrical stimulation pulses to brain tissue. Often, the electrical activity adjacent to one or several electrodes is analyzed to determine whether the recorded signals are consistent with the targeted region of the brain. If the recorded signals are not consistent with the targeted region, an adjustment to the lead's position can be made as appropriate.

After the correct location for the stimulation is established, an implantable pulse generator is implanted within a subcutaneous region and the stimulation lead is implanted underneath the skin and "tunneled" to the location of the pulse generator. The pulse generator is "programmed" to deliver electrical stimulation according to various stimulation parameters such as pulse amplitude, pulse width, pulse frequency, electrode configuration, etc. In conventional DBS therapies, stimulation is provided on a chronic basis. That is, electrical stimulation pulses are provided to the patient on a substantially continuous basis.

More recent DBS therapies have been proposed that utilize closed-loop feedback systems to control when to deliver electrical stimulation and to control the stimulation parameters. For example, a number of systems to treat epilepsy have been proposed in which electrical activity within various regions of the brain are sensed and electrical stimulation is applied when an epileptic event is imminent as indicated by frequency specific oscillations in the electrical activity. Closed-loop systems that measure neurotransmitter levels in lieu of electrical activity have been alternatively proposed. For Parkinson's disease, it has been proposed to measure the amount of extracellular glutamate in certain regions of the brain and control electrical stimulation applied to the thalamic tissue in response to the measured glutamate level. It has also been proposed to employ a closed-loop system to selectively apply electrical stimulation to a patient suffering from depression based upon the amount of serotonin in various regions of the brain. Appetite suppression using electrical stimulation to treat obesity is another therapy that could benefit from the measurement of neurotransmitter levels.

BRIEF SUMMARY

In one embodiment, a deep brain stimulation (DBS) system for electrically stimulating a target location in the brain of a patient, comprises: pulse generating circuitry for generating electrical pulses; at least one electrical lead for conducting electrical pulses generated by the pulse generating circuitry to the target location using one or several stimulation electrodes, wherein the at least one electrical lead further comprises one or several electrochemical sensors for sensing an extracellular level of one or several neurotransmitters and/or precursors; and a controller for controlling the pulse generating circuitry using closed-loop feedback based upon the extracellular level of the one or several neurotransmitters, wherein the controller for controlling the pulse generating circuitry processes the extracellular level of the one or several neurotransmitters using a measured impedance between one or several of the electrochemical sensors and a reference electrode.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is

DETAILED DESCRIPTION

One problem that has not been considered in the literature related to closed-loop systems for deep brain stimulation is the occurrence of post-traumatic cystic cavitation which is described in detail in CELLULAR AND MOLECULAR MECHANISMS OF GLIAL SCARRING AND PROGRESSIVE CAVITATION: IN VIVO AND IN VITRO ANALYSIS OF INFLAMMATION-INDUCED SECONDARY INJURY AFTER CNS TRAUMA, The Journal of Neuroscience, Oct. 1, 1999, 19(19):8182-8198, by Fitch et al. Specifically, when a conventional neurotransmitter sensor is implanted within the brain of a patient in an appropriate location, a small area of direct trauma is created by the insertion of the probe carrying the sensor through brain tissue. Even when minimally invasive techniques are employed for the implantation, in-vivo inflammatory processes alone initiate a cascade of secondary tissue damage, progressive cavitation, and glial scarring in the central nervous system. The initial site of the injury (e.g., the location of the neurotransmitter sensor) expands in size until a relatively large scar-encapsulated cavity is produced.

The encapsulation of the neurotransmitter sensor by scar tissue significantly reduces the sensor's sensitivity to the extracellular neurotransmitter level in the brain region of interest. Accordingly, after an amount of time from the implantation, the closed-loop system may be continuously operated upon an erroneous measurement of a low level of extracellular neurotransmitter and may, then, tend to apply stimulation at a maximum level without interruption. In essence, the closed-loop feedback control would cease functioning and the system would begin to function in the same manner as a chronic stimulation system.

Some representative embodiments operate the feedback loop of a closed-loop stimulation system to mitigate the effects of glial scarring. Specifically, some embodiments initially measure the impedance between a stimulation electrode of a DBS probe and the neurotransmitter sensor electrode of the DBS probe. The initial impedance is stored within the memory of the DBS implantable pulse generator (IPG). From time to time during operation of the IPG, the impedance between the stimulation electrode and the sensor electrode is measured. The relative impedance measurements (i.e., the original to the current impedance values) are used to calibrate the sensor measurement for closed-loop operation. In one embodiment, the ratio of the current impedance value to the original impedance value is used to scale the current neurotransmitter measurements for operation of the closed-loop system.

Figure 1:
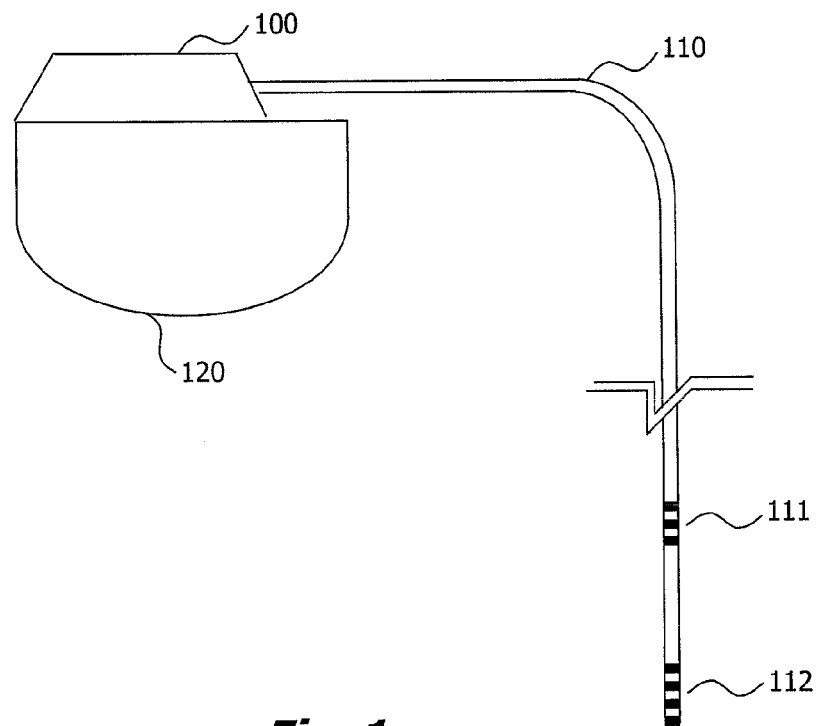
FIG. 1 depicts a stimulation system according to one representative embodiment.

Referring now to the drawings, FIG. 1 depicts stimulation system 100 according to one representative embodiment. Stimulation system 100 could be utilized to apply stimulation for any number of disorders such as Parkinson's disease, depression, obsessive-compulsive disorder, compulsive eating or other eating disorders, obesity, or any other disorder in which the level of a relevant neurotransmitter in a region of the brain is related to severity of the symptoms associated with the disorder. The relevent neurotransmitters may include, but are not limited to, dopamine, serotonin, glutamate, and/or any related precursor molecules.

Stimulation system 100 comprises pulse generator 120 and lead 110. Pulse generator 120 is adapted for implantation within a suitable subcutaneous region. Pulse generator 120 comprises a hermetically sealed housing which encloses the operational circuitry of generator 120. The operational circuitry 120 includes logic and/or program code for implementing a closed-loop for controlling the stimulation applied to a deep brain structure in a manner that compensates for the effects of glial scarring.

Stimulation lead 110 comprises stimulation electrodes 112 for delivering electrical pulses to the target brain tissue. Electrodes 112 are coupled to terminals (not shown) via respective wire conductors embedded in the insulative material of the lead body. Stimulation lead 120 further comprises neurotransmitter sensors 111 (electrochemical sensors). Neurotransmitter sensors 111 are utilized to detect a level of a specific neurotransmitter within an appropriate location within the brain. Neurotransmitter sensors 111 can be disposed immediately adjacent to or interleaved with stimulation electrodes 112. Alternatively, neurotransmitter sensors 111 can be disposed at a distance from stimulation electrodes 112 depending upon the relative positions of the target brain tissue for stimulation and the affected brain tissue in which the neurotransmitter is released in response to the stimulation.

Although only one stimulation lead is shown in FIG. 1, multiple stimulation leads or probes can be utilized according to some representative embodiments. For example, a lead could be utilized for sensors 111 that is separate from a lead utilized for stimulation electrodes 112. Also, multiple stimulation leads or sensing leads could be utilize to stimulate or sense in different regions.

Neurotransmitter sensors 111 can be implemented using suitable carbon fiber material. The conductivity, non-toxicity, and small size of carbon fiber microelectrodes enable the electrochemical detection of oxidizable compounds to occur. In particular, catecholamines (epinephrine, norepinephrine, and dopamine) and indolamines (serotonin and melatonin) are accurately measurable using carbon fiber microelectrodes using amperometric detection and differential pulse voltammetry. In particular, the carbon fiber electrodes enable an oxidation current to be measured when the released neurotransmitter is subjected to an applied voltage or current. Other neurotransmitters such as glutamate and acetylecholine can be measured in a similar manner using enzyme-modified carbon electrodes. The agent specific enzyme (for example, glutamate oxidase) is immobilized on the surface of an electrode and the by-product of an oxidation reaction is detected as an applied potential versus a reference electrode. Although carbon fiber sensors have been described, any suitable electrochemical sensor (now existing or later developed) can be utilized according to some representative embodiments.

Without being bound by theory, it is contemplated by representative embodiments that glial scarring acts as a resistance to the oxidation current that is detected by the carbon fiber electrochemical sensors. Accordingly, representative embodiments measure the resistance between the electrochemical sensors 111 by applying a potential difference between the sensors 111 and one or several stimulation electrodes 112. The change in the measured resistance over time is believed to be indicative of the reduction in chemical sensitivity of the sensors 111 due to inhibition of the oxidation current by glial scarring.

Figure 2:
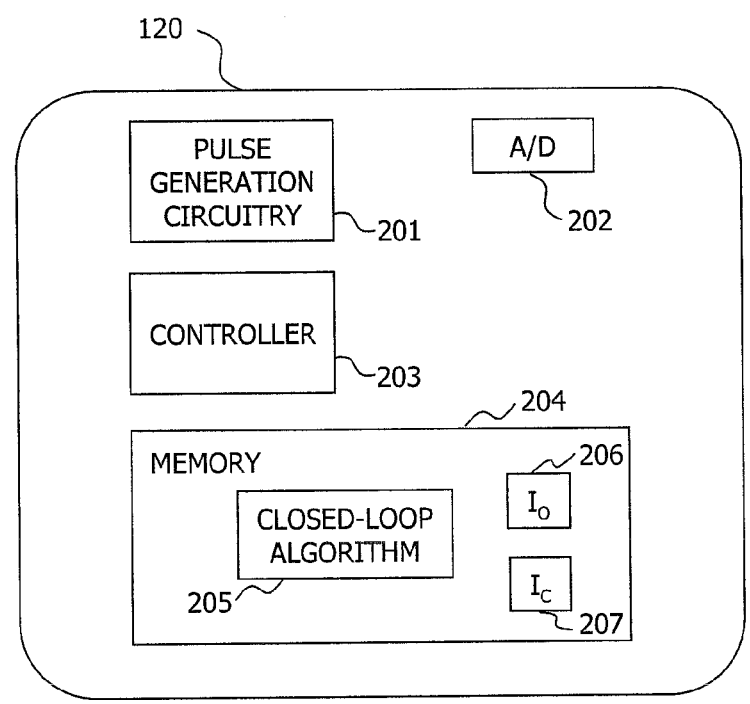
FIG. 2 depicts a pulse generator according to one representative embodiment.

FIG. 2 depicts a block diagram of pulse generator 120 according to one representative embodiment. Pulse generator 120 comprises pulse generation circuitry 201 for generating electrical pulses and applying the pulses to selected electrodes. Pulse generator circuitry 201 may utilize any suitable pulse generation design including constant voltage and constant current pulse generators as known in the art. Pulse generator 120 further comprises analog-to-digital (A/D) converter 202 for converting one or several physiological signals such as the neurotransmitter level detected by one or several of sensors 111 into digital form for processing by controller 203. Also, A/D converter 202 can be utilized for impedance measurements for processing by controller 203. Controller 203 may be implemented using a conventional microprocessor. Controller 203 preferably operates under the control of appropriate software instructions as retrieved from memory 204.

The software instructions include the software instructions defining closed-loop algorithm 205 for applying electrical stimulation to the target region of the brain. Closed-loop algorithm 205 utilizes impedance values $I_0$ 206 and $I_C$ 207. In one preferred embodiment, as the neurotransmitter level is determined using one or several sensors 111 and A/D converter 202, closed-loop algorithm 205 processes the neurotransmitter level utilizing the ratio of $I_C$ 207 to $I_0$ 206.

Impedance value $I_0$ 206 represents a baseline or reference impedance value. Impedance value 206 can be established using an appropriate default value that is typical of the initial impedance between a reference electrode 112 and a particular sensor 111. Alternatively, the impedance between the reference electrode 112 and the particular sensor 111 can be measured relatively soon after implantation of system 100 in the patient. From time to time, controller 203 determines the impedance between the reference electrode and the sensor 111 using A/D converter 202. Controller 203 stores the determined impedance value in the location associated with impedance value $I_C$ 207.

Figure 3:
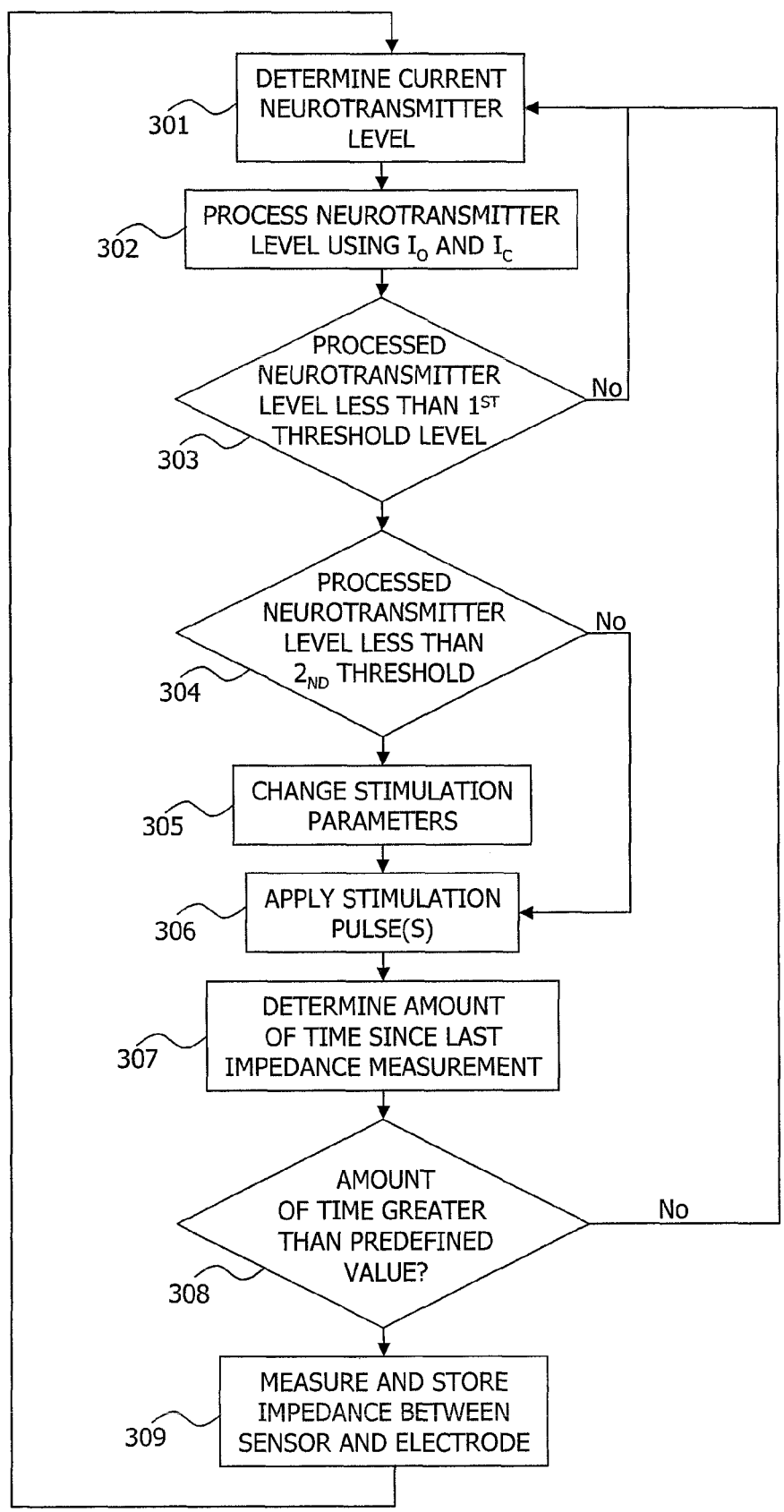
FIG. 3 depicts a flowchart for performing deep brain stimulation according to one representative embodiment.

FIG. 3 depicts a flowchart for operation of stimulation system 100 according to one representative embodiment. In step 301, the current extracellular neurotransmitter level in a region of the brain is determined using one or several sensors 111. In step 302, the measured neurotransmitter level 302 is processed using the impedance values $I_0$ 206 and $I_C$ 207. The processing may be a linear scaling operation or may employ a non-linear operation.

In step 303, a logical operation is made to determine whether the processed neurotransmitter level is less than a first threshold value. If neurotransmitter level is above the first threshold value, the processed neurotransmitter level is deemed within a "normal" range and the process flow returns to step 301. If the processed neurotransmitter level is less than the first threshold value, the processed neurotransmitter level is determined to be too low and the process flow proceeds to step 304.

In step 304, another logical operation is performed to determine whether the processed neurotransmitter level is less than a second threshold value. If not, the process flow proceeds to step 306. If the processed neurotransmitter level is less than the second threshold value, the processed neurotransmitter level is considered to be in significant deviation from a normal range and the stimulation parameters are adjusted to bring the neurotransmitter level into a desired range more quickly (step 305). In step 305, the stimulation amplitude and/or the stimulation pulse width may be increased to elicit a greater amount of neurotransmitter release in response to the stimulation. The increase of the stimulation parameter(s) may occur repeatedly over multiple iterations of the closed-loop. Also, the increase of the stimulation parameter(s) is preferably subjected to maximum parameter limits for safety purposes. In step 306, one or several stimulation pulses are delivered according to the current stimulation settings.

In step 307, the amount of time since the occurrence of the last impedance measurement is determined. In step 308, the amount of time is compared against a predetermined value (e.g., one day). If the predefined amount of time has not yet passed, the process flow returns to step 301. If the predefined amount of time has passed, the impedance between one or several sensor electrodes 111 and one or several stimulation electrodes 112 is measured and stored. After the impedance value is stored, the process flow returns to step 301.

Although some embodiments have been described in terms of deep brain stimulation, alternative embodiments may apply electrical stimulation to other brain regions. For example, an alternative embodiment may employ cortical stimulation where the stimulation electrodes are positioned extradurally or within the dura. Some embodiments of the invention may operate using any stimulation modality as long as an electrochemical sensor is positioned within the tissue of the brain where glial scarring may occur.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from this disclosure, processes, machines, manufacture, compositions of matter, means, methods, or steps, presently existing or later to be developed that perform substantially the same function or achieve substantially the same result as the corresponding embodiments described herein may be utilized without departing from the scope of the appended claims. Accordingly, the appended claims are intended to include within their scope such processes, machines, manufacture, compositions of matter, means, methods, or steps.

What is claimed:

1. A method of performing deep brain stimulation (DBS) of a target location in the brain of a patient, the method comprising:

implanting at least one stimulation lead in the brain of the patient, the at least one stimulation lead comprising one or several stimulation electrodes and one or several electrochemical sensors;

implanting a pulse generator within the patient and coupling the pulse generator to the at least one stimulation lead;

operating the pulse generator to stimulate the target location according to a closed-loop feedback, the operating comprising:

(i) measuring an impedance between one or several of the electrochemical sensors and a reference electrode by the pulse generator, wherein the reference electrode is one of the stimulation electrodes;

(ii) measuring an extracellular level of one or several neurotransmitters using one or several of the electrochemical sensors;

(iii) performing a correction operation on the measured extracellular level using the measured impedance and a previously stored impedance value to generate a feedback-loop parameter; and (iv) generating and delivering pulses in response to the generated feedback-loop parameter.

2. The method of claim 1 wherein the measuring the extracellular level measures an extracellular amount of dopamine.

3. The method of claim 1 wherein the measuring the extracellular level measures an extracellular amount of serotonin.

4. The method of claim 1 wherein the measuring the extracellular level measures an extracellular amount of glutamate.

5. The method of claim 1 wherein the DBS stimulation alleviates symptoms associated with Parkinson's disease.

6. The method of claim 1 wherein the DBS stimulation alleviates symptoms associated with depression.

7. The method of claim 1 wherein the DBS stimulation alleviates symptoms associated with a mood disorder.

8. The method of claim 1 wherein the DBS stimulation alleviates symptoms associated with an obsessive-compulsive disorder.

9. The method of claim 1 wherein the DBS stimulation alleviates symptoms associated with obesity.

10. The method of claim 1 further comprising:
    modifying a pulse amplitude or a pulse width depending upon the generated feedback-loop parameter.

* * * * *